United States Patent
Van Eikeren et al.

(10) Patent No.: US 7,789,662 B2
(45) Date of Patent: Sep. 7, 2010

(54) DENTAL MASKING PRODUCT FOR TEETH AND GUM

(75) Inventors: Andreas Van Eikeren, Cuxhaven (DE); Manfred Thomas Plaumann, Cuxhaven (DE)

(73) Assignee: VOCO GmbH, Cuxhaven (DE)

( * ) Notice: Subject to any disclaimer, the term of this patent is extended or adjusted under 35 U.S.C. 154(b) by 0 days.

(21) Appl. No.: 10/517,072

(22) PCT Filed: Jun. 18, 2003

(86) PCT No.: PCT/EP03/06433

§ 371 (c)(1), (2), (4) Date: May 10, 2005

(87) PCT Pub. No.: WO2004/032883

PCT Pub. Date: Apr. 22, 2004

(65) Prior Publication Data

US 2005/0221257 A1     Oct. 6, 2005

(30) Foreign Application Priority Data

Sep. 24, 2002     (DE) ................................ 102 45 274

(51) Int. Cl.
*A61C 5/14* (2006.01)
(52) U.S. Cl. ...................... 433/136; 433/215
(58) Field of Classification Search ................. 433/136, 433/215
See application file for complete search history.

(56) References Cited

U.S. PATENT DOCUMENTS

| | | | | |
|---|---|---|---|---|
| 4,204,324 | A * | 5/1980 | Kostner et al. | 433/229 |
| 4,538,920 | A * | 9/1985 | Drake | 366/181.5 |
| 4,559,013 | A * | 12/1985 | Amstutz et al. | 433/22 |
| 4,778,832 | A * | 10/1988 | Futami et al. | 523/109 |
| 5,059,121 | A * | 10/1991 | Schulz et al. | 433/88 |
| 5,371,162 | A * | 12/1994 | Konings et al. | 528/15 |
| 5,624,260 | A * | 4/1997 | Wilcox et al. | 433/90 |
| 5,661,222 | A * | 8/1997 | Hare | 525/478 |
| 5,676,543 | A * | 10/1997 | Dragan | 433/136 |
| 6,048,202 | A * | 4/2000 | Jensen et al. | 433/136 |
| 6,086,370 | A * | 7/2000 | Jensen et al. | 433/136 |
| 6,291,546 | B1 * | 9/2001 | Kamohara et al. | 523/109 |
| 6,305,936 | B1 | 10/2001 | Jensen et al. | 433/136 |
| 6,677,393 | B1 * | 1/2004 | Zech et al. | 524/366 |

FOREIGN PATENT DOCUMENTS

| | | |
|---|---|---|
| DE | 4306997 | 9/1994 |
| DE | 69512287 | 5/2000 |
| DE | 19915004 | 10/2000 |
| DE | 19959255 | 6/2001 |
| DE | 10105357 | 8/2002 |
| WO | 96/27342 | 9/1996 |

* cited by examiner

*Primary Examiner*—Ralph A Lewis
(74) *Attorney, Agent, or Firm*—Vidas, Arrett & Steinkraus

(57) ABSTRACT

Covering composition for isolating tooth material to be treated and producing a shield for the surrounding gums and/or adjacent teeth from dental treatment means which cross-links in a self-curing manner at an ambient temperature in the mouth interior and produces an elastomeric material.

12 Claims, No Drawings

DENTAL MASKING PRODUCT FOR TEETH AND GUM

CROSS-REFERENCE TO RELATED APPLICATIONS

This application is a 371 of PCT/EP03/06433 filed Jun. 18, 2003.

STATEMENT REGARDING FEDERALLY SPONSORED RESEARCH

Not Applicable

BACKGROUND OF THE INVENTION

The invention relates to a covering composition, a method and a device for isolating tooth material to be treated and producing a shield for the surrounding gums and/or adjacent teeth.

With some dental treatments, aggressive chemical substances are used in the mouth which can cause burning to the oral mucosa. Amongst these is the acid etching technique at the dental surgery, in the context of applying a composite filling and bleaching with preparations containing a high percentage of peroxide (in-office bleaching). With the acid etching technique the dental enamel is treated with a highly-concentrated, usually approximately 35 wt. % phosphoric acid within a prepared tooth cavity to improve the adhesion before the application of a primer and/or bonding. The phosphoric acid solution or phosphoric acid gel is then left to act for approximately 30 seconds on the dental enamel. In particular with preparations whose edges lie in the vicinity of the gum or an adjacent tooth, it is necessary for this tissue to be shielded from the etching means. It is further desirable to protect the treated tooth, or similarly a plurality of teeth, relative to the surrounding tissue of the oral cavity in a leak-tight fashion, to prevent, for example blood or saliva from reaching the treated tooth.

With the 'in-office' bleaching treatment, bleaching agents with a content of up to 35 wt. % hydrogen peroxide are directly applied onto the surface of the tooth to whiten the teeth. In particular when whitening vital teeth the bleaching agent is applied on the external surfaces of the tooth up to the vicinity of the gum margin. A protective cover of the oral mucosa is also imperative in this case to prevent burning.

A possibility for shielding consists in the use of a resilient sheet made from rubber which is referred to as a dental dam. The dentist then has to perforate the sheet at suitable points and punch out holes of a corresponding size in the sheet, through which the teeth to be treated are subsequently pushed. Where the size of the holes is unsuitable or where there are imperfections on the surface of the tooth, the problem frequently arises that the resilient sheet does not sit and seal precisely or tightly enough along the gum margin and thus does not sufficiently protect the oral mucosa. The positioning of a dental dam is regarded by many dentists as too costly and awkward. The danger arises that when stretched or during the treatment the rubber tears or loosens. As a result the isolating effect of the dental dam is lost and the material present on the exterior of the rubber sheet can enter the oral cavity. Patients find the cumbersome equipment and the fastening of the rubber on the neck of the tooth unpleasant.

In U.S. Pat. No. 6,305,936 compositions and methods are cited which are designed to overcome the above-mentioned disadvantages of the dental dam technique when sealing soft tissue parts in the mouth interior. A polymerisable material is protected in the Patent which comprises at least one monomer, a curing agent and at least one further compound. The compositions are conventional, light-curing acrylate systems which have to be considerably modified for use on soft tissues. As free-radical polymerisation of acrylates initiated by light releases a large amount of heat during cross-linking, when this system is used on oral soft tissue, such as for example the gums, a non-reactive additive such as mineral oil or polyol must be added to the mixture to ensure that the tissue of the patient does not suffer any burns. The addition of a plasticiser is therefore also necessary to reduce the cross-link density of the acrylate and thus to be able to ensure that the polymerised material can be removed again from the tissue after the treatment. By adding a reflective material, such as for example mica, a portion of the energy radiated by the polymerisation lamp into the mixture is intended to be reflected, thus to help reduce the resulting heat energy in the mixture.

Furthermore, the addition of a thickening agent to the polymerisable composition, such as for example xanthan gum, cellulose derivative, carboxypolymethylene, polyethylene oxide or high molecular weight polypropylene glycol is recommended in the Patent to provide it with muco-adhesive properties.

It can be seen that only by modifying the acrylate system at extremely high cost can a formulation be produced which corresponds to the most approximate criteria for the use of the formulation on soft tissues. A particular disadvantage of the invention moreover is that by using a plasticiser an attempt is made to reduce substantially the degree of polymerisation. A reduced degree of polymerisation allows the presence of either free monomers or corresponding oligomer structures of lower molecular weight. It is known that polymer compounds with a molecular weight of less than 1000 g/mol easily pass through biological membranes and bioaccumulate. (J H Hamilton, R Sutcliffe, Ecological Assessment of Polymers, 1996, Page 274). In the case of the very toxic acrylate components bis-GMA or HEMA, a reduced degree of polymerisation might consequently lead to cytotoxic problems when the invention is used. A further disadvantage is the time-consuming use of irradiation with a polymerisation lamp. As a result, depending on the width of the light outlet window, each piece has to be polymerised for 20 seconds, piece by piece.

The object of the present invention is therefore to provide a covering composition, a method and a device for isolating a tooth material to be treated and producing a shield for the surrounding gums and/or adjacent teeth from dental treatments which, relative to the prior art, can be more rapidly applied and are more comfortable and less toxic to use.

BRIEF SUMMARY OF THE INVENTION

It has been found that at ambient temperature self-curing systems which cure to an elastomeric material, fulfill the object very well. Preferably it refers to systems which are mixed to a homogenous composition immediately before and/or when applying a plurality of components, preferably two components. By ambient temperature the range between normal room temperature (15-25° C.) and mouth temperature (ca. 37° C.) is understood. According to the invention, the curing starts spontaneously in this temperature range immediately after mixing the components without the addition of energy through light or heat being necessary.

The substance class of so-called 'cold-curing', addition-cross-linking silicones (RTV-2 A-silicones) proves to be particularly suitable. The material is preferably applied as a paste in the mouth and by cross-linking changes from a spreadable consistency into the rubber-elastic state. The cross-linked material surprisingly adheres to the gum and due to its elastomeric property can easily be pulled off the substrate in one piece after the treatment and removed from the mouth. The adhesion of the silicone to the gums, which is excellent for the inventive purpose and which is even observed when the soft tissues are relatively dry by using only a cotton swab and an air blower, presents a completely unexpected finding, as a pronounced strong hydrophobia is a general and characterising feature of silicone. By strong hydrophobia is understood the effect that water in the fluid phase does not wet or only wets very slightly the silicone/air interface. As the gums, like all other soft tissue parts of the mouth interior, are permanently covered with a characteristic film of moisture, it should be expected that a hydrophobic material would show no adhesion to the soft tissues due to insufficient wetting.

The hydrophobia of the cured surfaces of the silicones promotes the sealing and covering effect relative to conventional hydrophilic treatments such as bleaching and etching agents. Moreover they are neutral in taste and smell, physiologically harmless and can be adjusted over very short curing times. Relative to acrylates, the substance class of the prior art, they are not obviously exothermic during the curing process and show no measurable reduction in size.

Further suitable substance classes for a covering composition for isolating tooth material to be treated and producing a shield for the surrounding gums and/or adjacent teeth from dental treatments are condensation cross-linking silicones (C-silicones) and polyether materials, as are described in DE 4306997.

Mixing the components takes place either manually on a mixing block with a spatula or preferably automatically with the aid of a cartridge system with a static mixing tube for direct application. With the preferably used direct application of the silicone compositions the two components must then be filled into a double chamber cartridge. The application is then carried out by pressing out the pastes from the double chamber cartridge with the aid of a double plunger through a static mixing cannula onto the tissue to be protected of the mouth interior. A different colouring of the two unmixed initial compositions enables the homogenity of the mixture to be verified after the passage of the paste through the mixing cannula on the basis of the resulting colour tone. The chemical curing begins immediately after the application of the pastes onto the tissue and is completed within a short time.

The mixture ratio of the two components can be between 1:10 and 10:1 and preferably lies between 1:4 and 4:1 and particularly preferably between 2:1 and 1:2.

If the covering compositions according to the invention are used in a double chamber cartridge with a static mixing cannula for an impermeable covering of teeth and/or gums in the mouth interior, then the advantageous properties of this method of use are revealed:

Due to their adjustable rheological properties they can be applied easily and precisely, they exhibit good flow-on behaviour, and ensure a good seal, in particular at the gum margin (neck of the tooth, papillae). The consistency and sufficient length of time for workability allow adjustments to be made during the application of the pastes and ensure that the material has not already cured in the mixing cannula during the application. After the application rapid curing takes place in the mouth, so that immediately after the application further treatment can be continued without the necessity of a waiting period or an additional working step such as light curing.

With addition-cross-linking silicones, curing generally takes place by a platinum-catalysed addition reaction of Si—H functional polysiloxanes to polysiloxane with unsaturated hydrocarbon groups, generally vinyl or allyl groups. The silicone compositions are normally used as a two component system. The synthesis of the individual components takes place in such a manner that each component is in itself not reactive and therefore stable. The storage stability of the silicone compositions is thus ensured by a separation of Si—H functional polysiloxane and the platinum catalyst. As a rule the one component contains a vinyl functional polydimethylsiloxane, a filler and a Si—H functional polydimethylsiloxane, whilst the other component also contains a vinyl-functional polydimethylsiloxane, a filler and a platinum catalyst. The fluidity of the pastes is governed by the contents of the filler and the viscosity of the polysiloxane used. When using a cartridge system for automatic metering and mixing of the components the ability of the components to be easily pressed out and mixed has to be ensured which can advantageously be achieved by similar viscosities of the polysiloxane mixtures and similar filler contents in the components. Additionally, thixotroping agents, pigments, dyes, plasticisers, stabilisers, emulsifiers, hydrophilic agents, reaction inhibitors, hydrogen absorbers or fixing agents can be used as additives. The fillers used in the composites can have absorption properties (such as diatomite, zeolite, calcium carbonate), reinforcing properties of the material (silicas) or non-reinforcing properties of the material (quartz, cristobalite, aluminium oxide, zinc oxide). Thixotroping agents, such as pyrogenic silicas, polymeric polyalkylene oxide or cellulose derivatives, govern the stability of the mixture, whilst plasticisers (including paraffin, tallow, wax) stabilisers, emulsifiers and hydrophilising agents can ensure the correct handling and stability properties. Hydrophilising agents ensure improved wettability of the mixture on the damp soft tissues of the mouth and produce improved flow behaviour of the pastes. Suitable additives are ethoxylated fatty alcohols and polyalkylene glycol esters or polyalkylene glycol ethers.

The vinyl-functional polydimethylsiloxanes are preferably of linear composition and comprise end groups of dimethylvinylsiloxane units. If a higher degree of cross-linking is to be reached, compounds are used which have more than two vinyl groups per molecule, the vinyl groups then being able to be distributed across the molecular structure. The crosslinker is an organohydrogenpolysiloxane with at least three Si—H groups per molecule. Additionally organohydrogenpolysiloxanes with two Si—H groups per molecule can be used as so-called chain extenders to influence the curing behaviour and the mechanical strength. The volume ratios of vinyl-functional polydimethylsiloxane to organohydrogensiloxane are generally selected so that 1 to 3 mol of Si—H units are available per mol of unsaturated groups.

The catalyst used has to catalyse the reaction between the Si—H groups and the vinylsiloxane. It is known to use platinum or palladium compounds to this end. A frequently used catalyst is a platinum complex which is produced from hexachloroplatinic acid by a reduction with tetramethyldivinyldisiloxane and is used in a volume of 4 to 400 ppm, preferably between 20 and 50 ppm, as elemental platinum and relative to the total weight of the mixture.

EXAMPLE

Component 1 (Basic Paste)

23 parts of a vinyl-terminated polydimethylsiloxane with a viscosity of 1000 mPas, 3 parts of a polydimethylsiloxane containing Si—H groups with a Si—H content of 4.2 mmol/g, 4 parts of a surface-treated pyrogenic silica (Aerosil R 972, Degussa A G) and 0.1 parts of a yellow coloured pigment (Sicomet S10, BASF) are mixed homogenously in a kneader.

Component 2 (Catalyst Paste)

26 parts of a vinyl-terminated polydimethylsiloxane with a viscosity of 1000 mPas, 0.15 parts of a solution of a complex of platinum and divinyldimethylsiloxane, which contains 1.0 wt. % platinum in a vinyl-terminated polydimethylsiloxane with a viscosity of 1000 mPas, 4 parts of a surface-treated pyrogenic silica (Aerosil R 972, Degussa A G) and 0.1 parts of a white coloured pigment (titanium dioxide) are mixed homogenously in a kneader.

The basic and catalyst pastes are respectively filled in one chamber of a 5 ml double syringe with a volume ratio of 1:1 (Mixpac Systems AG) free of air bubbles. After holding away the lips of the patient and brief drying of the application area by means of an air blower the application takes place by a suitable mixing attachment applied directly onto the oral mucosa in the immediate vicinity of the area to be treated. The paste emerges homogenously mixed from the mixing attachment in a consistency which allows a smooth coating of the tooth to be treated and exhibits a flow-on behaviour which ensures a secure seal and adhesion on the oral mucosa. After the brief flow-on phase the material has a stability which prevents the material from running down or spreading and allows a precise application. The curing allows rapid application of the continuous coating of an entire row of teeth without the blocking of the mixing cannula, the paste still being able to be moved and easily spread with the cannula tip during the application. The curing takes place at mouth temperature approximately 5 seconds after mixing and is so far advanced within 10 seconds that the composition has solidified as rubber-elastic and further treatment can be begun immediately. After the treatment the cured silicone is easily removed in one piece without leaving any residue.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. Method for isolating tooth material to be treated with liquid dental treatment means to protect the surrounding gingiva from the liquid dental treatment means, comprising the steps of:
    providing a covering composition which cross-links in a self-curing manner at an ambient temperature in the mouth interior on the gingiva and produces an elastomeric material which adheres to the gingiva, wherein the covering composition is selected from the group consisting of A-silicones, C-silicones or polyethers;
    applying the covering composition in a flowable state onto the gingiva around, below but not onto the tooth material to be treated, the covering composition after cross-linking in a self-curing manner at ambient temperature adhering to the gingival, and
    applying a liquid dental treatment to the tooth material to be treated.

2. Method according to claim 1, in which the covering composition is produced by mixing a multiple-component system.

3. Method according to claim 2, in which the covering composition is produced by mixing a two-component system.

4. Method according to claim 2, wherein the covering composition immediately after mixing has a rheological flow-on behaviour when applied in the mouth and within one second after application has such a stability that the applied composition does not run down or spread.

5. Method according to claim 2, wherein the cross-linking begins within 20 seconds after mixing the components and is so far advanced within 40 seconds after mixing the components that the composition is solidified as rubber-elastic.

6. Method according to claim 2, wherein the cross-linking begins within 10 seconds after mixing the components and which is so far advanced within 20 seconds after mixing the components that the composition is solidified as rubber-elastic.

7. Method according to claim 2, wherein the cross-linking begins within 5 seconds after mixing the components and is so far advanced within 10 seconds after mixing the components that the composition is solidified as rubber-elastic.

8. Method according to claim 1, wherein the cross-linked covering composition can be easily removed in one piece from the mouth without leaving any trace.

9. Method according to claim 1 in which the area of application is dried before the application of the covering composition.

10. Method according to claim 1, in which the components are mixed with one another before and/or during the application of the covering composition.

11. Method according to claim 1, further comprising applying the covering composition to teeth adjacent to the tooth material to be treated.

12. Method for protecting gingiva from a liquid dental treatment means applied to tooth material adjacent to the gingiva comprising the steps of:
    applying a covering composition to gingiva, the covering composition cross-linking in a self-curing manner at an ambient temperature in the mouth to produce an elastomeric material that adheres to the gingiva, the elastomeric material protecting the gingiva from a liquid dental treatment means applied to tooth material adjacent to the gingiva, the covering composition being applied to the gingiva in a flowable state, the covering composition being selected from the group consisting of A-silicones, C-silicones, or polyethers, and
    applying a liquid dental treatment to the tooth material.

* * * * *